(12) United States Patent
Fischer et al.

(10) Patent No.: US 9,050,080 B2
(45) Date of Patent: Jun. 9, 2015

(54) MULTIFUNCTIONAL ELEMENT AND METHOD TO PREVENT THE CARBONIZATION OF TISSUE BY MEANS OF A MULTI-FUNCTIONAL ELEMENT

(75) Inventors: Klaus Fischer, Nagold (DE); Alexander Neugebauer, Moessingen (DE); Markus Enderle, Tuebingen (DE); Matthias Zenker, Tubingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 475 days.

(21) Appl. No.: 13/395,367

(22) PCT Filed: Sep. 7, 2010

(86) PCT No.: PCT/EP2010/005484
§ 371 (c)(1),
(2), (4) Date: Mar. 9, 2012

(87) PCT Pub. No.: WO2011/029572
PCT Pub. Date: Mar. 17, 2011

(65) Prior Publication Data
US 2012/0172874 A1 Jul. 5, 2012

(30) Foreign Application Priority Data

Sep. 11, 2009 (DE) .......................... 10 2009 041 167

(51) Int. Cl.
*A61B 18/18* (2006.01)
*A61B 18/04* (2006.01)
*H05H 1/24* (2006.01)

(52) U.S. Cl.
CPC ................ *A61B 18/042* (2013.01); *H05H 1/24* (2013.01)

(58) Field of Classification Search
CPC .................. A61B 2018/00601; A61B 18/042; A61B 2018/00589
See application file for complete search history.

(56) References Cited

U.S. PATENT DOCUMENTS

| 6,582,427 | B1 | 6/2003 | Goble et al. |
| 2004/0116918 | A1 | 6/2004 | Konesky |
| 2007/0029500 | A1 | 2/2007 | Coulombe et al. |
| 2009/0039790 | A1 | 2/2009 | Suslov |
| 2010/0114092 | A1* | 5/2010 | Eisele et al. .................... 606/41 |
| 2011/0139751 | A1* | 6/2011 | Koo et al. ........................ 216/67 |

FOREIGN PATENT DOCUMENTS

| DE | 195 16 238 A1 | 11/1996 |
| DE | 697 18 466 T2 | 11/2003 |
| DE | 699 17 073 T2 | 4/2005 |
| DE | 10 2007 025 551 A1 | 12/2008 |
| EP | 0 740 926 A2 | 11/1996 |
| EP | 1 829 492 A1 | 9/2007 |
| EP | 2 160 081 A1 | 3/2010 |

(Continued)

*Primary Examiner* — Christopher D Koharski
*Assistant Examiner* — Philip Edwards
(74) *Attorney, Agent, or Firm* — Dickstein Shapiro LLP

(57) ABSTRACT

A multi-functional element suitable for performing at least two surgical/therapeutic interventions, for example, the injection and cutting of tissue, with an anti-carbonization device to prevent the carbonization of tissue upon plasma coagulation by way of a suitable surgical instrument, where the surgical instrument has a feed line for an oxidizing agent, a feed line for a gas and an electrode for generating a plasma. A gas oxidizing agent mixture for producing a gas oxidizing agent plasma is provided by the anti-carbonization device.

16 Claims, 7 Drawing Sheets

(56) References Cited

FOREIGN PATENT DOCUMENTS

| | | |
|---|---|---|
| JP | 2001-178740 A | 7/2001 |
| JP | 2008-543355 A | 12/2008 |
| RU | 2 161 931 C2 | 1/2001 |
| RU | 2 195 226 C2 | 12/2002 |
| WO | WO 03/084294 A1 | 10/2003 |
| WO | WO 2006/108480 A1 | 10/2006 |
| WO | WO 2006/119892 A1 | 11/2006 |
| WO | WO 2008/090004 A1 | 7/2008 |
| WO | WO 2009/146432 A1 | 12/2009 |

* cited by examiner

MULTIFUNCTIONAL ELEMENT AND METHOD TO PREVENT THE CARBONIZATION OF TISSUE BY MEANS OF A MULTI-FUNCTIONAL ELEMENT

FIELD OF THE INVENTION

Embodiments of the invention relate to a multifunctional element suitable for performing at least two surgical/therapeutic interventions, a method to prevent the carbonization of tissue upon plasma coagulation as well as the use of a multifunctional element.

BACKGROUND

High-frequency (HF) surgery, of which plasma coagulation is a subset, has been used for many years, both in human medicine and in veterinary medicine, to coagulate and/or cut biological tissue. Suitable electrosurgical instruments are used to pass high-frequency current through the tissue to be treated, so that this tissue changes as a result of protein coagulation and dehydration. Vessels can be sealed and bleeding stopped through this coagulation process. A cutting process that follows the coagulation process enables full separation of tissue that has already coagulated.

Plasma coagulation enables a non-contact coagulation of tissue and serves for effective haemostasis and devitalization of tissue. In this type of coagulation, inert working gas, for example argon, is passed via gas supply devices from a plasma coagulation instrument to the tissue to be treated. With the help of the working gas, a "plasma jet" can be generated between an electrode at a distal end of the gas supply device, such as a probe, and the tissue. The HF current can then be applied to the tissue to be treated without the electrosurgical instrument coming into contact with the tissue. This therefore avoids adherence of the tissue to the instrument.

Furthermore, with resection of tissue, in particular tumor tissue in the gastrointestinal tract, which is limited to the mucosa, it should be ectomized in a single session and as completely as possible. To enable tumors that have a large surface area with a diameter of more than eight centimeters to be ectomized in one session and as completely as possible, it is proposed in WO 2006/108480 A1, for example, that for endoscopic mucosal resection, prior to resection, the mucosa is first injected with liquid using a flexible needle. The needle is thereby placed in the submucosa. The penetration of the liquid into the mucosa causes it to separate from the muscularis propria, with a fluid cushion forming beneath the mucosa: This creates a safety distance from the muscularis propria, and confers thermal protection. Mucosal resection is then carried out, for example, with a flexible needle knife, but in particular with the above-described HF surgical instrument.

With a water jet surgical instrument according to the prior art, a bundled water jet is discharged at a distal end of the instrument at high pressure which penetrates the soft mucosa. The penetrating liquid is collected in the submucosa (in the resilient fibrous displacement layer) such that a fluid cushion forms.

The above-described treatments can also result in internal bleeding, which obstructs the view of the surgeon, so that the operating site has to be rinsed. A suitable rinsing probe is generally provided for this purpose.

A disadvantage of the above-described procedures is that a separate instrument is required for each one, necessitating a time-consuming change of the respective instrument for each new intervention. Furthermore, plasma coagulation that is gentle to tissue is only possible at low power and/or with short application times, since at higher power levels carbonization of coagulated tissue cannot be reliably ruled out. The carbonization can lead to inflammation of the tissue and an increase in post-operative problems. The generation of smoke and plume, which is accompanied by an unpleasant odor, is also not ruled out with certainty with carbonization. Moreover, the smoke obscures the vision of the surgeon and for this reason must be avoided. Another disadvantage is the development of concentrated current paths during plasma coagulation, resulting in inhomogeneous damage to tissue. Lastly, oozing bleeding that can occur during the intervention is difficult to localize using the known instruments.

SUMMARY

The aim of embodiments of the invention is therefore to provide a multi-functional element and method to prevent the carbonization of tissue by a multi-functional element, with which at least two surgical/therapeutic interventions can be carried out, where the multi-functional element enables optimal treatment of the patient and improved handling.

The aim is achieved by a multi-functional element suitable for performance of at least two surgical/therapeutic interventions, for example for injection and for cutting tissue. It can preferably also coagulate tissue. It has an anti-carbonization device to prevent the carbonization of tissue during plasma coagulation by a suitable surgical instrument. The surgical instrument comprises a feed line for an oxidizing agent, a feed line for a gas and an electrode to generate a plasma, where the anti-carbonization device provides a gas-oxidizing agent mixture to generate a gas-oxidizing agent plasma. The multifunctional element thus enables the performance of at least two surgical/therapeutic interventions; in particular, a plasma coagulation and application of water, in particular the injection of tissue, whereas a separate instrument is normally required for each intervention so that a change of the respective instruments is necessary. Moreover, the use of an anti-carbonization device makes it possible to ensure an optimal tissue-conserving treatment of the patient, since a carbonization of the tissue and the associated disadvantages are avoided. Furthermore, the anti-carbonization device ensures a reduction of smoke/plume, significantly improving the view of the surgeon and dispensing with the need to ventilate the operating room. The multi-functional element can further deploy a liquid medium for rinsing purposes, for example water, a physiological saline solution or the like. This enables, for example, oozing bleeding to be more readily recognized and to be stopped directly with plasma surgery or electrosurgery.

Overall, the multi-functional element proposed here enables a tissue-conserving haemostasis and tissue-conserving devitalization of tumor tissue. Furthermore, it is particularly advantageous that thin-walled and/or nerve-sensitive structures can be readily treated as well. In addition, the multi-functional element can be used in a particularly advantageous manner for low-adhesion coagulation in open surgery, for laparoscopy and for flexible endoscopy. The anti-carbonization device of the multi-functional element furthermore reduces carbonization of tissue during plasma coagulation, so that improved wound healing conditions result. The anti-carbonization device enables coagulation with lower odor generation and the coagulation of tissue with low smoke and plume is thus possible. Since the multi-functional element can be used not just for HF surgical interventions, but also for water applications, for example contact-free injection of liquid to form a liquid cushion (needle-free injection) in the sub-mucosal layer of the mucous membrane to build a thermal protective cushion, the tissue surface can be treated with a standard plasma coagulation without destruction of deeper-lying tissue layers. At the same time, the multi-functional element enables flushing of the surgical site to improve visibility if there is bleeding, without necessitating the use of a separate instrument.

The use of the multi-functional element can be particularly advantageous in flexible endoscopy, but it is also conceivable to use the multi-functional element for open surgery and laparoscopy. The anti-carbonization device of the multifunctional element is particularly advantageous in endoscopic applications, since a change of instrument is rarely necessary and the unavoidable obstruction of view through plume development is virtually absent during plasma treatment.

Particularly preferred is an embodiment of the multi-functional element, where the oxidizing agent used for the anti-carbonization device is liquid or gaseous. Water is preferably used as the oxidizing agent and an inert gas, in particular argon, as the gas. The oxidizing agent may also be in the form of an aerosol, so that it is thus atomized into fine droplets of the oxidizing agent to form an oxidizing agent mist. The oxidizing agent mist increases the specific surface and thus the heat exchange surface between the oxidizing agent and the carrier gas by more than a hundredfold, so that the evaporation point of the liquid oxidizing agent droplets is substantially reduced and the oxidizing agent mist therefore evaporates substantially faster. As a result, a substantial proportion of the oxidizing agent is in the form of an oxidizing agent vapor. This allows a proportion of the oxidizing agent, namely that portion in the form of a gas, to be ionized to an oxidizing agent vapor plasma. This forms a reactive plasma, which in the case of water as the oxidizing agent contains species such as $H_2O^+$, H, OH and O radicals. By increasing the specific surface, the tissue surface can, moreover, be cooled markedly, which reduces carbonization. It is also conceivable to convert the oxidizing agent prior to provision of the gas-oxidizing agent mixture into its gaseous state using an evaporator. Furthermore, nanoparticles with particular properties can be mixed into the oxidizing agent, for instance to intensify or accelerate a therapeutic effect or reduce side-effects. It is conceivable, for example, to mix in nanoparticles that have a positive effect on the wound healing process.

Further preferred is an embodiment of the multi-functional element, where the surgical instrument to generate the aerosol has an evaporator. Furthermore, instead of an evaporator, an ultrasound generating device can be provided to generate the aerosol. Alternatively, however, a baffle may be provided, against which the oxidizing agent impacts, so that it is atomized upon rebounding from the surface. In this manner, the gas-oxidizing agent mixture can be provided in a particularly simple way by the anti-carbonization device.

An embodiment of a multi-functional element is also preferred which is characterized in that at least one two-substance atomization device/two-substance nozzle is provided. This may have internal or external mixing. With a two-substance atomization device it is possible in a simple manner to provide a gas-oxidizing agent mixture for generation of a gas-oxidizing agent plasma.

Furthermore, an embodiment of a multi-functional element is preferred, which is characterized in that the surgical instrument has a jacket that has at least one opening in the region of the electrode to prevent a gas embolism. This at least substantially reduces the probability of a gas embolism or emphysema development upon contact of the jacket with the tissue.

Finally, an embodiment of a multi-functional element is preferred that has a fluid applicator for injection of tissue with a liquid. The multi-functional element can be used to carry out treatment with a water jet as well as a cutting procedure, or for plasma coagulation, without requiring a change of the surgical instrument. The fluid applicator can also be used to clean the surgical site. The oxidizing agent of the anti-carbonization device is preferably supplied to the fluid applicator for injection of tissue. The oxidizing agent is then preferably present as a liquid; in particular the oxidizing agent is water.

Furthermore, a self-aspirating two-substance atomization device can be provided, which is preferably created by the arrangement of the gas supply channel and the oxidizing agent supply channel and which makes an additional pump for the supply of the oxidizing agent unnecessary.

The aim of the embodiments of the present invention is also achieved by a method for preventing the carbonization of tissue upon plasma coagulation by a multi-functional element, where the multi-functional element has an anti-carbonization device to prevent the carbonization of tissue during plasma coagulation by a suitable surgical instrument. The surgical instrument further has a feed line for an oxidizing agent, a feed line for a gas and an electrode to generate a plasma. The process is characterized by the step of provisioning a gas-oxidizing agent mixture to generate a gas-oxidizing agent plasma.

The advantageous method described herein enables a substantial reduction in the carbonization of tissue since the carbon formed is oxidized by the oxidizing agent. In addition, the surface of the tissue is cooled at the same time by the oxidizing agent. Particularly preferred is an oxidizing agent, which is liquid or gaseous. However, the oxidizing agent may also be provided as an aerosol. In this case, the surgical instrument preferably has a corresponding device for generating the aerosol. The oxidizing agent must be suitable for the oxidation of carbon, which is the case, for example, with water. An inert gas, in particular argon, is preferred as the gas.

The aim of the invention is ultimately achieved through the use of a multi-functional element according to the features of claim 20. The use of a multi-functional element with an anti-carbonization device provides a gas-oxidizing agent mixture to generate a gas-oxidizing agent plasma, resulting in an effective reduction in the carbonization of tissue.

BRIEF DESCRIPTION OF THE DRAWINGS

Hereinafter, exemplary embodiments of the invention are explained in greater detail with reference to drawings, in which.

DETAILED DESCRIPTION

Figure 1:
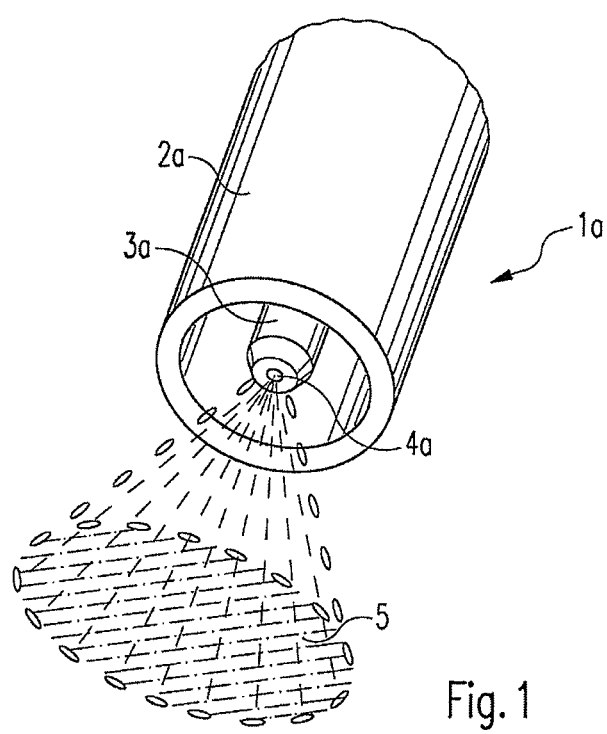
FIG. 1 is a schematic perspective view of a first surgical instrument.

FIG. 1 shows a schematic perspective view of a first surgical instrument 1a. The instrument 1a has a jacket 2a that envelops an electrode 3a, which is connected to a high-frequency generator that supplies a high-frequency current to the electrode 3a. The electrode 3a serves at the same time as a supply channel for a liquid component, which emerges from the electrode 3a in the region of a centrally-arranged discharge opening 4a.

The surgical instrument 1a according to FIG. 1 enables, for example, for an endoscopic submucosal dissection (ESD), injection of the tissue with the water jet emanating from the electrode 3a and thus separation of the mucosa from the muscularis. An incision or dissection of the injected tissue can subsequently be performed.

FIG. 1 makes it clear that the liquid component exits the electrode 3a in the form of an expanded, in particular conical, turbulent water jet 5. It can, moreover, be used not just for the injection of the mucosa, but also to flush the surgical site so that the surgeon has a clear view of the surgical field.

Figure 2:
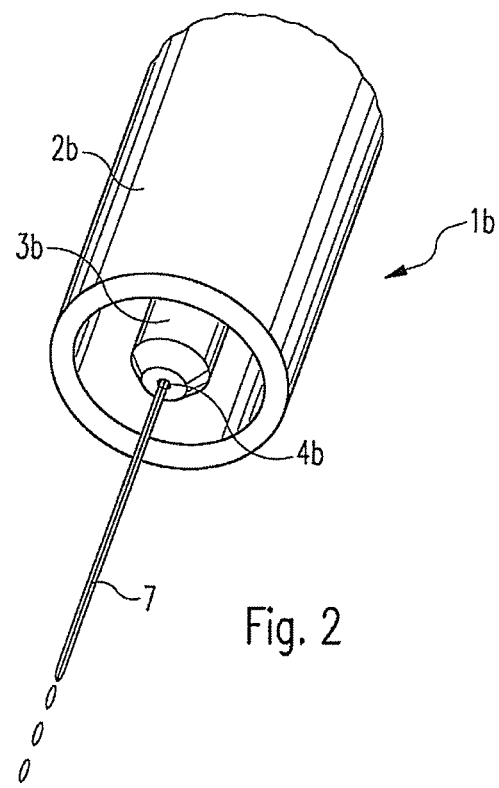
FIG. 2 is a schematic perspective view of a second surgical instrument.

FIG. 2 shows a schematic perspective view of a second surgical instrument 1b with a jacket 2b and an electrode 3b disposed therein. This instrument 1b has a supply channel for a liquid component, where the supply channel is provided with a centrally-disposed discharge opening 4b, from which the liquid component emerges in the form of a laminar jet 7 that preferably serves for the needle-free injection of a liquid, particularly water, into the submucosa as a protective cushion in the dissection of the mucosa.

It is clear that the surgical instrument 1b differs from the surgical instrument 1a shown in FIG. 1 solely in terms of the shape of the emerging liquid jet. This can be changed through the shape of the discharge region 4a/4b and be adapted to the properties of the tissue to be treated.

Figure 3:
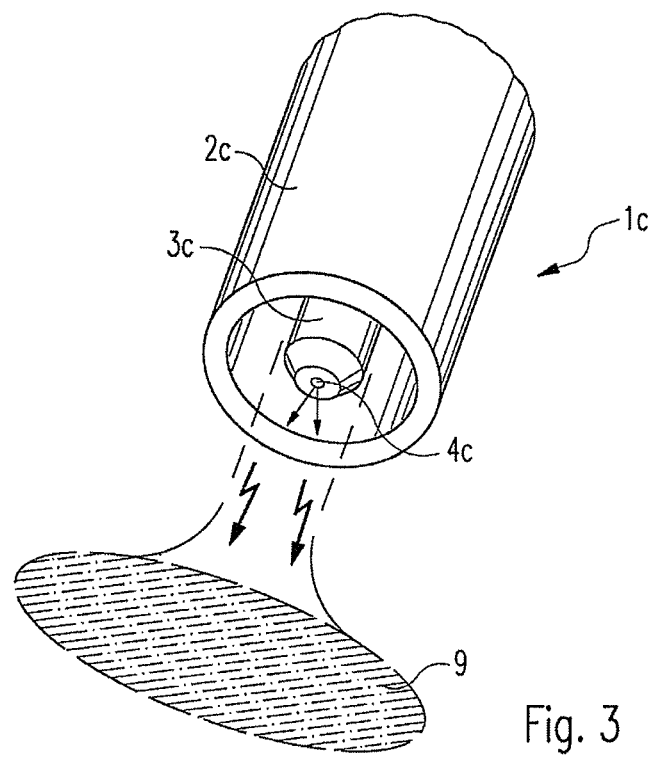
FIG. 3 is a schematic perspective view of a third surgical instrument.

FIG. 3 shows a schematic perspective view of a third surgical instrument 1c with a jacket 2c and an electrode 3c disposed therein, around which, internally and/or externally, a noble gas, in particular argon, flows. Such a surgical instrument 1c is used in plasma coagulation, in particular in argon plasma coagulation. The electrode 3c is in turn connected to a HF generator that supplies a high-frequency current to the electrode.

FIG. 3 clearly shows that the noble gas in the vicinity of a discharge opening 4c of the electrode 3c is ignited by the high-frequency alternating electric field, so that a noble gas plasma 9 is generated between the electrode 3c of the surgical instrument 1c and a layer of tissue (not shown).

Figure 4:
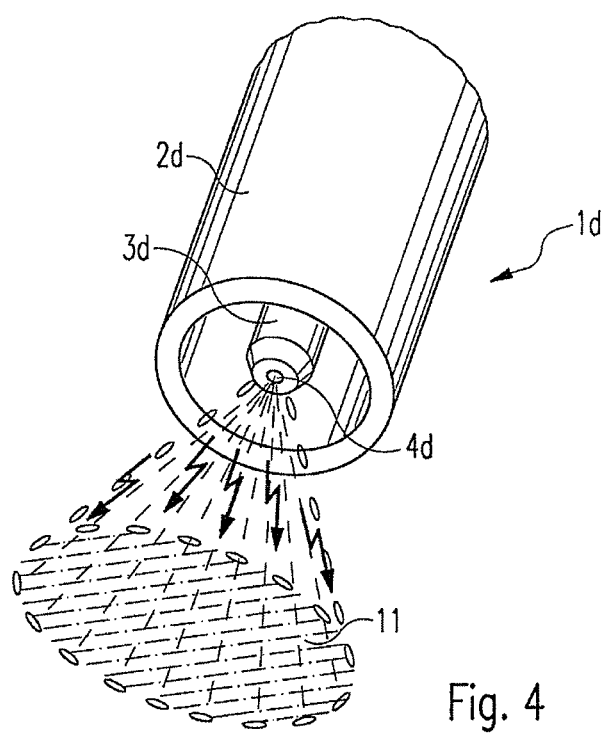
FIG. 4 is a schematic perspective view of a fourth surgical instrument.

FIG. 4 shows a schematic perspective view of a fourth surgical instrument 1d with a jacket 2d and an electrode 3d arranged therein, which is connected to a HF generator and has a supply channel with a discharge opening 4d. A gas-oxidizing agent mixture flows through the supply channel and emerges in the region of the discharge opening 4d in the form of a cone-shaped jet 11 and is ignited by the high-frequency alternating electric field to a gas-oxidizing agent plasma.

The surgical instrument 1d thus has an anti-carbonization device that provides a gas-oxidizing agent mixture for generation of a gas-oxidizing agent plasma, the advantages of which will be explained in more detail below. The anti-carbonization device prevents carbonization of the tissue to be treated and associated smoke and plume development is avoided in an advantageous manner.

Figure 5:
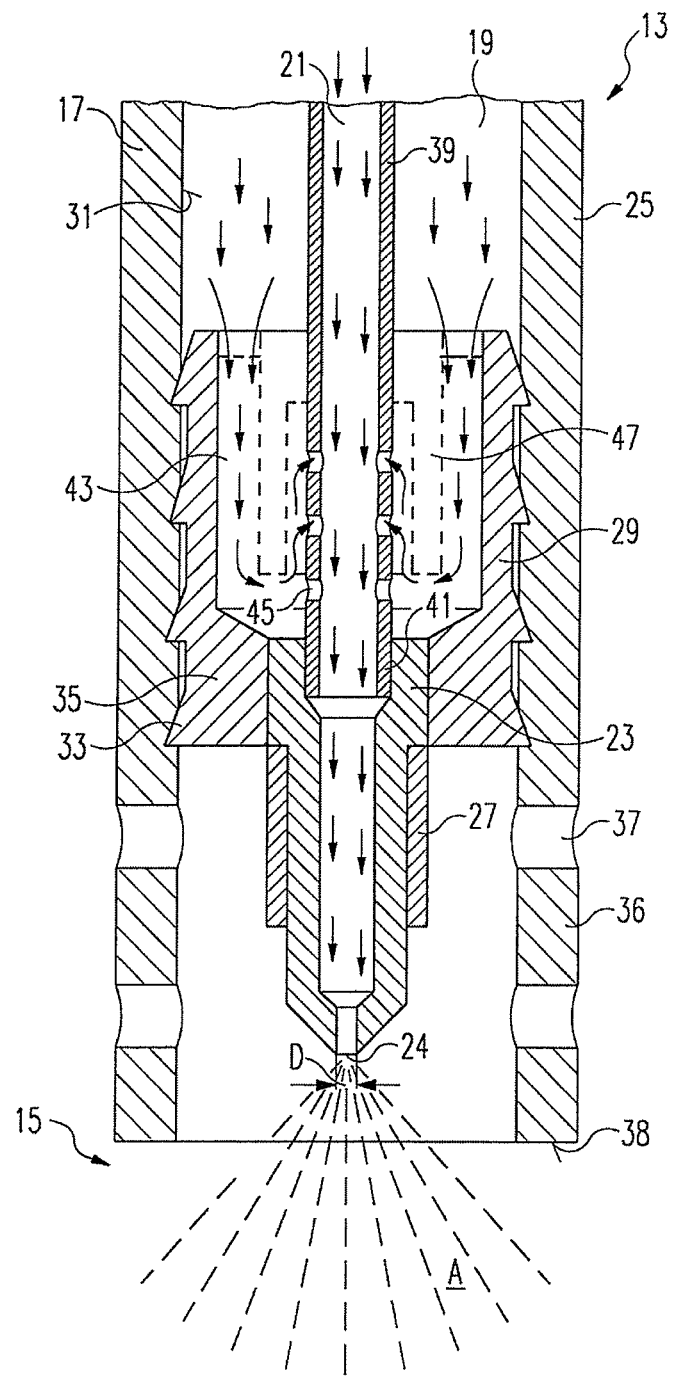
FIG. 5 is a schematic sectional view of a first embodiment of a multi-functional element.

FIG. 5 shows a schematic sectional view of a first multi-functional element 13 according to an embodiment of the invention. The multi-functional element 13 comprises an anti-carbonization device 15, which reduces carbonization of coagulated tissue, where plasma coagulation is performed by a suitable surgical instrument 17.

As explained in more detail below, the multifunctional element 13 combines the functions of surgical instruments 1a to 1d shown in FIGS. 1 to 4 in an advantageous manner. It is thus possible with the multi-functional element 13 described herein to mark and elevate the tissue to be treated by its injection, then perform an incision/dissection of the tissue and eventually bring about a low-carbonization coagulation, whilst additionally cleaning the surgical site through the multi-functional element 13.

FIG. 5 makes it clear that the surgical instrument 17 has a supply channel 19 for a gas, hereinafter referred to as gas supply channel 19, and a supply channel 21 for an oxidizing agent, hereinafter referred to as oxidizing agent supply channel 21. Furthermore, an electrode 23 is provided, which supplies a high-frequency current from a HF voltage source (not shown). The electrode 23 is hollow and has a discharge opening 24. Thus, the electrode 23 serves as a form of extension of the oxidizing agent supply channel 21.

The gas supply channel 19, the oxidizing agent supply channel 21 and the electrode 23 according to FIG. 5 are surrounded by a jacket 25, which is preferably comprised of PTFE and which is connected to a HF surgical device (not shown).

A protective insulation 27 is provided, which envelops the electrode 23 coaxially at least in part. A fixing sleeve 29 is provided within the jacket 25, which is secured to an inner wall 31 of the jacket 25 by way of suitable locking projections 33 and which envelops the electrode 23 with its distal region 35.

The distal end 36 of the jacket 25 enveloping the electrode 23 further has lateral openings 37 through which the gas-oxidizing agent mixture can escape, to enable the avoidance of a gas embolism and emphysema development if the jacket 25 lies with its front face 38 against the tissue to be treated.

The oxidizing agent supply channel 21 is formed in a pipe 39 that is preferably comprised of stainless steel, in particular V2A steel. The pipe 39 is connected at a proximal end, not shown, to a HF voltage source and thus serves at the same time as an electrical conductor, which supplies the electrode 23 with a high-frequency current. For this purpose, a distal end 41 of the pipe 39 is connected to the electrode 23.

Furthermore, the pipe 39 is connected to an oxidizing agent source (not shown) so that an oxidizing agent can pass through the pipe 39/through the oxidizing agent supply channel 21 and can further pass through the electrode 23 to the discharge opening 24 of the electrode 23.

An annular space 43 is provided between the fixing sleeve 29 and the pipe 39 into which the gas is passed from the gas supply channel 19. Furthermore, the pipe 39 in the region of the annular space 43 has at least one opening, in this case a plurality of openings 45, through which the gas from the annular space 43 can flow into the oxidizing agent supply channel 21. A diffuser 47, which is only represented in FIG. 5 by dashed lines, can further be arranged in the annular space 43.

The gas supply channel 19 and the oxidizing agent supply channel 21 of the surgical instrument 17 together form a two-substance nozzle, which is internal-mixing in the illustrated embodiment as an example only, so that the gas and the oxidizing agent are fed separately to a mixing chamber; where the mixing chamber in the present embodiment of the multi-functional element 13 is formed by the oxidizing agent supply channel 21. Only after mixing is the gas-oxidizing agent mixture passed through the discharge opening 24 outwardly into a discharge region A, where the discharge opening 24 in the electrode 23 quasi forms a nozzle. The discharge opening 24 can for this purpose have a specific inner diameter D and a suitable shape to generate a desired jet width of the ejected gas-oxidizing agent mixture. In FIG. 5, the discharge opening 24 is formed such that the jet has a conical shape.

The gas-oxidizing agent mixture upon emergence from the oxidizing agent supply channel 21 is preferably atomized such that the oxidizing agent/gas-oxidizing agent mixture in the discharge region A is present as an aerosol. To carry out plasma coagulation, the electrode 23/multifunctional element 13 is brought into the vicinity of the tissue to be treated and the emerging atomized gas-oxidizing agent mixture is ignited by the electrode 23/high-frequency current present there so that a conductive gas-oxidizing agent plasma is generated, through which the high-frequency current from the electrode 23 can flow to the tissue to bring about coagulation there.

The above-described multi-functional element 13 can thus, among other things, be advantageously used for plasma coagulation, especially for argon plasma coagulation. The multi-functional element 13 has an anti-carbonization device 15, which almost completely avoids carbonization of the tissue during the plasma coagulation. Argon is preferably used as gas and is fed through the gas supply channel 19, the annular space 43 and the openings 45 to the oxidizing agent. Any substance that is suitable for oxidation of carbon can be used as the oxidizing agent. However, water is preferably used as an oxidizing agent which oxidizes the carbon formed during the plasma coagulation.

The oxidizing agent can be passed in liquid or gaseous form into the oxidizing agent supply channel 21. It is also conceivable for the oxidizing agent to be a solid. If the oxidizing agent is passed into the oxidizing agent supply channel 21 in liquid form, then it is preferable for the oxidizing agent to be converted into an aerosol by any suitable mechanism. The oxidizing agent can also be converted into the respective gaseous substance, where the gaseous oxidizing agent is previously generated, for example through an evaporator.

In the embodiment according to FIG. 5, by way of example, the oxidizing agent is fed in liquid form through the oxidizing agent supply channel 21 and is mixed with the gas from the gas supply channel 19. The gas-oxidizing agent mixture is then fed to the discharge opening 24 of the electrode 23. In this way, the gas-oxidizing agent mixture is atomized so that it is present after emerging from the electrode 23 as an aerosol, where it is ignited by the HF current to form a plasma. Thus, a gas-oxidizing agent plasma is provided.

FIG. 5 clearly shows that not only an oxidizing agent-gas mixture can be passed through the oxidizing agent supply channel 21, but it can also serve for the feeding of an injection liquid for injection of tissue. The oxidizing agent can thereby serve as an injection liquid.

The multi-functional element 13 consequently has a water applicator through the oxidizing agent channel 21 that can bring about an injection of tissue to generate a liquid cushion under the tissue area to be ablated. The water applicator can be used, at the same time, for cleaning the surgical site if there is bleeding to ensure a free field of view for the surgeon.

The multifunctional element 13 shown in FIG. 5 can thus be used for three substantially different surgical/therapeutic interventions. First, the realization of a fluid cushion in the submucosal layer of the mucous membrane for the purpose of building a thermal protective cushion is possible. In this case, gas supply through the gas supply channel 19 is preferably switched off so that only the oxidizing agent, in particular water, is passed through the oxidizing agent supply channel 21. Furthermore, the multi-functional element 13 can be used to cut tissue by way of the electrode 23 and plasma coagulation can be performed. For this purpose, a noble gas, especially argon, is passed through the gas supply channel 19 into the discharge region A of the electrode 23, where the high-frequency current at the electrode 23 ignites a plasma between the electrode and the tissue.

Lastly, the multi-functional element 13 can advantageously generate an aerosol plasma by way of an anti-carbonization device 15. The multifunctional element 13 thereby reduces carbonization of the tissue during plasma coagulation and associated smoke and plume development. As a result, post-operative problems of the patient are firstly eliminated and secondly a reduction in visibility during the operation is prevented so that the anti-carbonization device 15 of the multifunctional element 13 brings substantial advantages for both the patient and the surgeon.

Finally, the oxidizing agent supply channel 21 can serve additionally as a supply channel for a flushing agent, which serves to clean the operating site.

Overall, the multifunctional element 13 of the type disclosed herein enables three main surgical/therapeutic interventions, for which a separate instrument would usually be necessary. The different functions of the multifunctional element 13 can moreover be advantageously activated with the optimized setting parameters, independently of one another where possible, for example via a footswitch or instrument handles.

Figure 6:
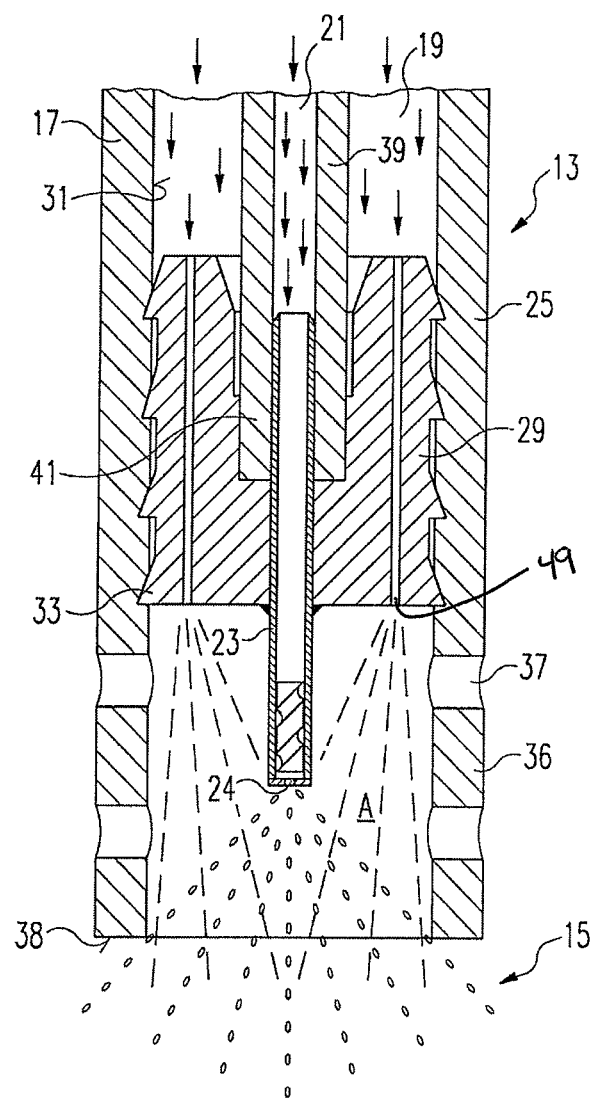
FIG. 6 is a schematic sectional view of a second embodiment of a multi-functional element.

FIG. 6 shows a schematic sectional view of a second embodiment of a multi-functional element 13 with an external-mixing two-substance nozzle, using a preferably spiral-shaped fixing sleeve 29 for the atomization of the two-substance liquid. The same parts are designated by the same reference numerals, so that where reference is made to the description of FIG. 5, repetition is avoided.

The surgical instrument 17 according to FIG. 6 in turn has a gas supply channel 19 that is enveloped by an oxidizing agent supply channel 21, where the two feed channels are formed in the jacket 25. It is clear that the arrangement of the oxidizing agent supply channel and the gas supply channel is an example only. It is also conceivable for the gas supply channel to be surrounded by the oxidizing agent supply channel.

According to the embodiment shown in FIG. 5, as already explained above, the fixing sleeve 29 is provided, and is arranged coaxially in the jacket 25 and is secured with suitable locking projections 33 to the inner wall 31 of the jacket 25. The jacket 25, in turn, has lateral openings 37 to prevent a gas embolism.

Furthermore, the electrode 23 is substantially centrally mounted in the fixing sleeve 29 and connected to the pipe 39, which serves as the oxidizing agent supply channel 21. The electrode 23 is hollow and serves quasi as an extension of the oxidizing agent supply channel 21. The distal end of the electrode 23 in the embodiment according to FIG. 6 also has a discharge opening 24 formed as a nozzle with a suitable diameter and has a suitable shape so that the oxidizing agent passed into the oxidizing agent supply channel 21 is atomized when it leaves the channel.

In contrast to the embodiment of the multi-functional element 13 shown in FIG. 5, in FIG. 6 the two-substance nozzle formed by the gas supply channel 19 and the oxidizing agent supply channel 21 has an external-mixing form. Thus, the gas and the oxidizing agent are not fed into a common mixing chamber and then atomized, instead the gas and the oxidizing agent are introduced into two separate channels externally and only after emerging from their respective supply channels 19, 21 do they form a gas-oxidizing agent mixture in the discharge region A.

For this purpose at least one axial through-hole 49 is provided in the fixing sleeve 29 to connect the gas supply channel 19 to the discharge region A, into which the electrode 23 extends.

The sectional view of FIG. 6 shows, purely as an example, two through-holes 49. It is obvious that more than two through-holes may be provided. It is also conceivable, however, to provide an annular space or the like or for the fixing sleeve 29 to be in two parts, so that the gas passes through the annular space in the discharge region A.

The gas-oxidizing agent mixture is therefore only made available in the discharge region A, and not already in the oxidizing agent supply channel 21 according to FIG. 5. It is also possible for the gas and the oxidizing agent to interact in the discharge region A at the distal end of the electrode 23 such that upon collision of the gas and the oxidizing agent there is atomization of the oxidizing agent. An atomization nozzle is therefore not required.

It should be noted that with the embodiment according to FIG. 6, the oxidizing agent may be liquid or gaseous. For example, it is conceivable to pass the oxidizing agent already in gaseous form through the oxidizing agent supply channel 21. The oxidizing agent in the discharge region A, however, is preferably in the form of an aerosol. To generate an aerosol, the surgical instrument 17 preferably has an evaporator or heater. Further, an aerosol can be generated by an ultrasound generation device. It is also conceivable, however, to use a baffle surface against which the oxidizing agent rebounds and is atomized.

Figure 7:
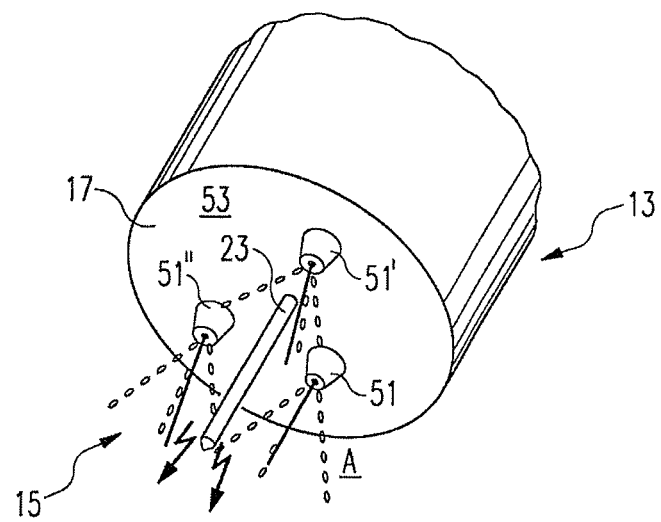
FIG. 7 is a schematic sectional view of a third embodiment of a multi-functional element.

FIG. 7 shows a third embodiment of a multi-functional element 13, where the surgical instrument 17 has a centrally-disposed rod-shaped electrode 23 that projects from the surgical instrument 17.

There are three two-substance nozzles, not shown in detail, arranged around the electrode 23 that have three discharge openings 51, 51' and 51". For example, the surgical instrument 17 can have the form shown in FIG. 5 or FIG. 6, where instead of one two-substance nozzle a total of three internal-mixing or external-mixing two-substance nozzles are provided. The gas-oxidizing agent mixture or the oxidizing agent then flows out of the discharge openings 51, 51' and 51". The discharge openings 51, 51' and 51" are preferably formed such that the gas-oxidizing agent mixture is atomized so that it is in the form of an aerosol in the discharge area A. Moreover, the base body 53 of the surgical instrument 17 is formed so that it is preferably electrically insulating.

Figure 8:
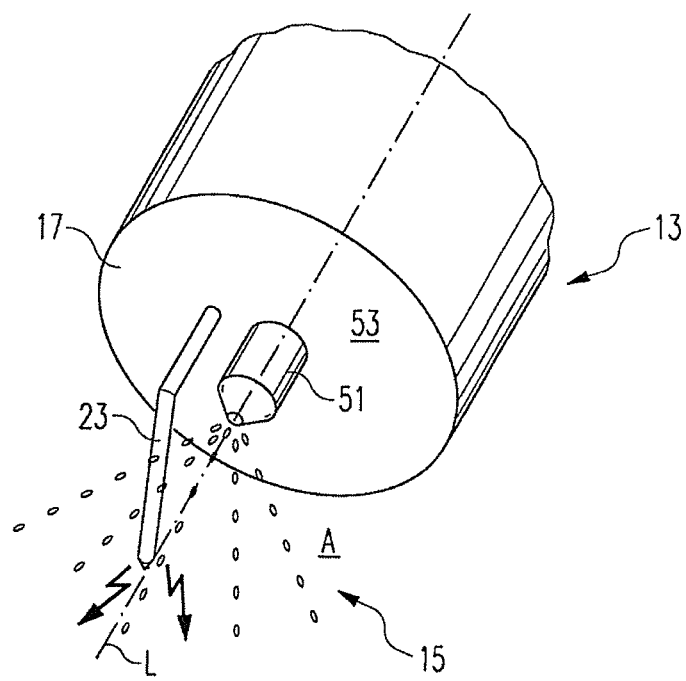
FIG. 8 is a perspective view of a fourth embodiment of a multi-functional element.

FIG. 8 shows a perspective view of a fourth embodiment of a multi-functional element 13. The same parts are designated by the same reference numerals, in so far as reference is made to the description for the preceding Figures, to avoid repetition.

In FIG. 8, the electrode 23 is arranged eccentrically with respect to the surgical instrument 17 and extends into the discharge region A. An outlet port 51 of a two-substance nozzle, not shown in detail here, is however arranged centrally with respect to the surgical instrument 17. The two-substance nozzle may be formed in this embodiment with internal or external mixing. For example, it is conceivable that with an internally-mixing two-substance nozzle according to the embodiment shown in FIG. 5, a gas oxidation mixture flows out of the discharge opening port 51, while with an externally-mixing two-substance nozzle the gas flows out of the discharge opening for example and the oxidizing agent flows out of the discharge opening 51, so that the gas-oxidizing agent mixture is provided only in the discharge region A.

FIG. 8 clearly shows that the electrode 23 is angled or bent such that it projects from its eccentric discharge position into the region of a longitudinal axis L of the multi-functional element 13/discharge opening 51. Moreover, the base body 53 of the surgical instrument 17 is formed so that it is preferably electrically insulating.

Figure 9:
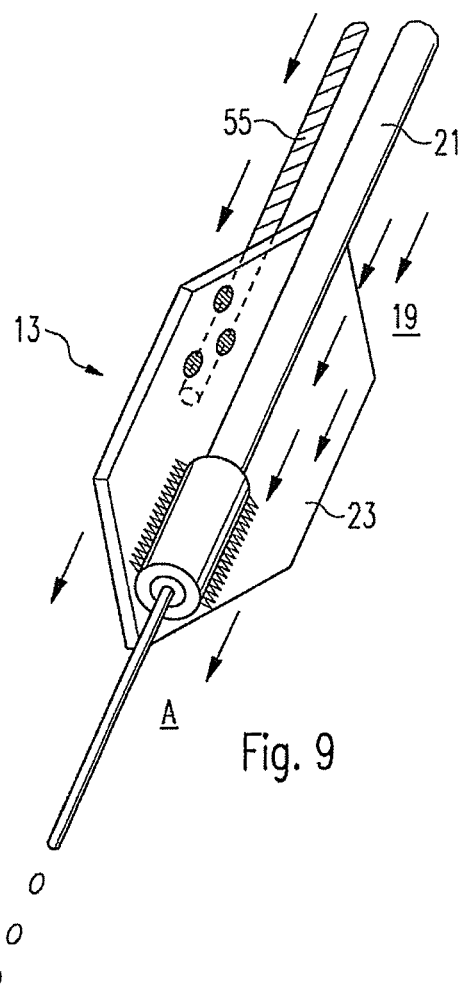
FIG. 9 is a schematic view of an electrode and a two-substance nozzle.

FIG. 9 shows a schematic representation of an embodiment of a two-substance nozzle of a multi-functional element 13 with an electrode 23. The same parts are designated by the same reference numerals, in so far as reference is made to the description of the preceding figures, to avoid repetition.

The two-substance nozzle according to FIG. 9 is formed with external mixing. The electrode 23 is also formed as a metal plate with an electrical lead 55 that is connected to a high-voltage source, not shown, which supplies a high-frequency current to the electrode 23. The metal plate is enveloped by a gas supply channel 19, so that the gas flows past the metal plate.

The oxidizing agent supply channel 21 is substantially parallel to the electrode 23, i.e., it is secured to the metal plate and generates a laminar jet, provided that the oxidizing agent is a liquid. The gas-oxidizing agent mixture is then made available in the discharge region A to generate a gas-oxidizing agent plasma.

Figure 10:
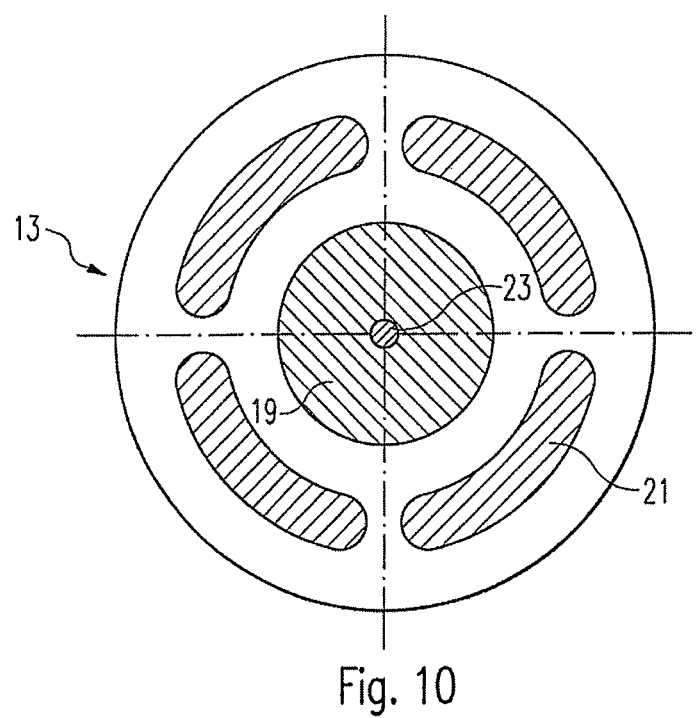
FIG. 10 is a top view of a discharge region of a surgical instrument.

FIG. 10 shows a top view of a multi-functional element 13. The same parts are designated by the same reference numerals, in so far as reference is made to the description of the preceding figures, to avoid repetition.

An external-mixing two-substance nozzle system is shown in FIG. 10, where the electrode 23 is arranged centrally and is enveloped by the gas supply channel 19. Four kidney-shaped oxidizing agent supply channels are provided coaxially and symmetrically to the gas supply channel 19 and can be arranged, for example, in the jacket 25 or in a fixing sleeve. A gas supply channel 19 is further provided coaxially to the electrode 1.

Figure 11:
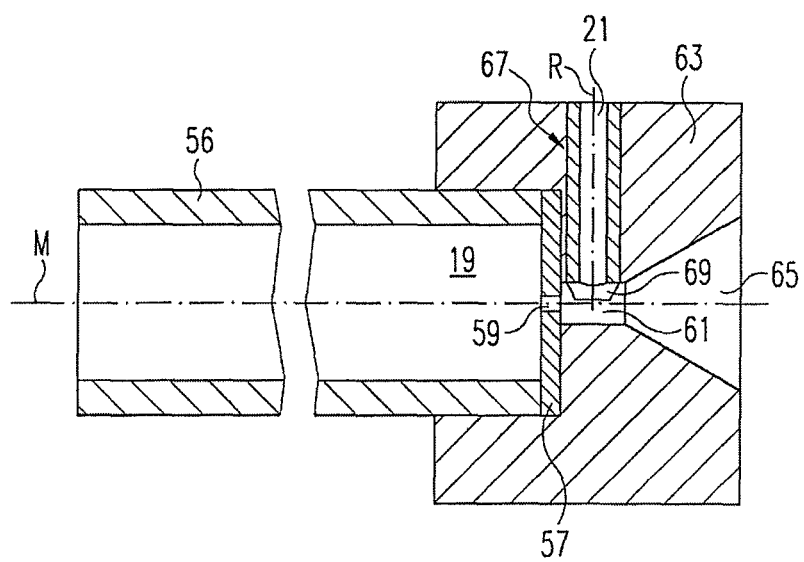
FIG. 11 is a schematic sectional view of an embodiment of a surgical instrument with Venturi nozzle.

FIG. 11 shows a further embodiment of the invention in which a gas-oxidizing agent mixture/an aerosol-oxidizing agent plasma or gas-oxidizing agent plasma is generated by the principle of a (gas) jet pump i.e., by the Venturi principle, whereby negative pressure is generated through constriction of a supply channel. Such jet pumps are generally known. The basic principle of such pumps is that a liquid or gaseous jet exits a nozzle at high speed and carries with it liquid, gas or solid from the surrounding area and accelerates it.

In accordance with the embodiments of the invention, a gas supply channel 19 for a gas that has a wall 56 may be provided, in particular for argon. The gas preferably flows through an aperture 57 arranged at the distal end of the gas supply channel 19 and in particular through a central discharge opening 59 in the aperture 57 into a cylindrical mixing region 61 of a top section 63, where the top section 63 is arranged at the distal end of the gas supply channel 19. The top section 63 may be formed integrally with the gas supply channel 19 or with its wall. It is, however, also conceivable for the top section 63 to be formed as a separate part and to be connected to the gas supply channel 19 in a suitable manner, in particular by gluing, soldering or the like. A frustoconical atomization region 65 adjoins the cylindrical mixing area 61 and is similarly centrally formed in the top section 63.

FIG. 11 clearly shows that the gas supply channel 19, opening 59, mixing region 61 and the atomization area 65 extend along a central axis M, and are substantially symmetrically arranged to it in sequence. An oxidizing agent supply pipe 67 extends along a radial axis R transversely to the central axis M, in which an oxidizing agent supply channel 21 is provided. The oxidizing agent supply pipe 67 is connected to a source of oxidizing agent (not shown). The oxidizing agent supply pipe 67 is inserted in a corresponding through-hole in the top section 63 that extends radially along the axis R or is integral with it and opens with its end section 69 into the distal cylindrical mixing region 61.

The principle of function of the embodiment according to FIG. 11 is as follows: at the bottleneck in the cylindrical mixing region 61 behind the opening 59, the static pressure of the gas, for energy conservation reasons, has to be lower than in the non-constricted parts of the device. As a result of the gas flow in the gas supply channel 19/mixing region 61, an oxidizing agent to be atomized, in particular water, is aspirated from the oxidizing agent supply channel 21 by the negative pressure in the mixing region 61 and is entrained in the gas stream. It is therefore an (external mixing) self-aspirating two-substance nozzle/Venturi nozzle, which has the advantage that a separate pump is not required for the supply of the oxidizing agent. Rather, the oxidizing agent is drawn into the mixing region 61 automatically through the gas flow. The gas supply channel 19 and the oxidizing agent supply channel 21 in this embodiment of the invention are therefore advantageously formed as a self-aspirating two-substance atomization device or as an (external-mixing) Venturi nozzle.

The desired gas-oxidizing agent mixture, in particular as an aerosol, is present in the atomization region 65 commencing from the mixing region 61, and a gas-oxidizing agent plasma is ignited by a suitable electrode.

The gas-oxidizing agent mixture of the aforementioned type has at least two components, where one component is a gas, in particular a noble gas such as argon or helium, and the other component is an oxidizing agent for carbon. The oxidizing agent may consist of solid or liquid suspended particles, for example, small water droplets, which are present as water mist. The liquid oxidizing agent is atomized very finely so that its surface area is greatly enlarged. In this way, the evaporation is greatly accelerated, so that in addition to the liquid oxidizing agent droplets, a significant proportion is present as oxidizing agent vapor. The high-frequency alternating current can also ionize oxidizing agent molecules, in particular water molecules, in the gas phase to form a water vapor-plasma mixture.

The above description makes it clear that the gas-oxidizing agent mixture is preferably an aerosol, which therefore has gaseous particles and finely-atomized oxidizing agent droplets. The aerosol plasma enables carbonization of the tissue to be largely avoided, where the oxidizing agent mist, in particular the water mist, i.e., the $H_2O$ droplets, at the same time acts as an oxidizing agent for carbon, as a coolant for the tissue surface and as plasma medium.

Furthermore, the significant reduction in carbonization is directly connected to the emission quantities of carbon black and gases such as $CO_2$, $CO$, $NO$, $NO_x$ and $SO_x$, as well as organic and biochemical molecules, so that the proposed device and the corresponding method lead to a significant reduction in the above-mentioned emissions and thus reduce the exposure risks of the patient and surgical personnel.

Moreover, the proposed anti-carbonization device enables a homogeneous, tissue-conserving coagulation and devitalization, with the aim of deploying the method in a tissue-preserving manner preferably in the field of oncosurgery, but also in other medical disciplines, for example for tumor ablation, especially in thin-wall and nerve-sensitive structures, in neurosurgery, urology and as an adhesion-reducing surgical method in gynecology and visceral surgery, both open surgery and endoscopic (rigid and flexible).

Furthermore, at least one two-substance nozzle can be provided, which can be of internal-mixing or external-mixing design. In addition, the surgical instrument 17 can have a suitable mechanism, for example an evaporator, an ultrasonic generator or a baffle plate, to generate an oxidizing agent aerosol/gas-oxidizing agent aerosol. The oxidizing agent can be atomized either before or after being mixed with the gas. The sole decisive aspect is that the gas contains liquid oxidizing agent droplets to bring about the advantages described above.

The anti-carbonization device 15 of the multi-functional element 13 thus effectively reduces carbonization and the development of carbon black and smoke. Furthermore, it achieves a more uniform distribution of the plasma energy over the tissue surface.

Overall, the embodiments of the present invention provide a multi-functional element 13 with an anti-carbonization device 15, with which a number of interventions can be advantageously performed without the need for an instrument change. Moreover, the anti-carbonization device 15 of the multi-functional element 13 provides a gas-oxidizing agent mixture for generation of a gas-oxidizing agent plasma. This enables a reduction in carbonization during the plasma coagulation.

The above advantages are also achieved by a method which provides a gas-oxidizing agent mixture for the performance of a plasma coagulation. The same applies with regard to the use of an anti-carbonization device 15 to prevent carbonization of the tissue.

The invention claimed is:

1. A surgical instrument suitable for performing at least two surgical/therapeutic interventions, said surgical instrument comprising:
a plasma coagulation device,
a fluid applicator for cutting and/or injecting tissue with fluid, and
an anti-carbonization device to prevent the carbonization of tissue upon plasma coagulation by the plasma coagulation device, the surgical instrument having a feed line for an oxidizing agent, a feed line for a gas and an electrode for generating a plasma,
wherein the anti-carbonization device provides a gas-oxidizing agent mixture for generating a gas-oxidizing agent plasma.

2. The surgical instrument of claim 1, wherein the at least two surgical/therapeutic interventions comprise injection and cutting of tissue.

3. The surgical instrument of claim 1, wherein the oxidizing agent is liquid.

4. The surgical instrument of claim 1, wherein the oxidizing agent is gaseous.

5. The surgical instrument of claim 1, wherein the oxidizing agent is an aerosol.

6. The surgical instrument of claim 5, further comprising an evaporator for generating the aerosol.

7. The surgical instrument of claim 5, further comprising an ultrasound generating device for generating the aerosol.

8. The surgical instrument of claim 5, further comprising a baffle plate for generating the aerosol.

9. The surgical instrument of claim 1, wherein the oxidizing agent is water.

10. The surgical instrument of claim 1, wherein the gas is an inert gas.

11. The surgical instrument of claim 10, wherein the inert gas is argon.

12. The surgical instrument of claim 1, further comprising a two-substance atomization device.

13. The surgical instrument of claim 12, wherein the two-substance atomization device is an internal-mixing device.

14. The surgical instrument of claim 12 wherein the two-substance atomization device is an external-mixing device.

15. The surgical instrument of claim 1, further comprising a jacket, which in a region of the electrode has at least one opening to prevent a gas embolism.

16. The surgical instrument of claim 1, further comprising a self-aspirating two-substance atomization device.

* * * * *